United States Patent
Brysch et al.

(10) Patent No.: US 6,365,345 B1
(45) Date of Patent: *Apr. 2, 2002

(54) ANTISENSE NUCLEIC ACIDS FOR THE PREVENTION AND TREATMENT OF DISORDERS IN WHICH EXPRESSION OF C-ERBB PLAYS A ROLE

(75) Inventors: Wolfgang Brysch, Göttingen; Karl-Hermann Schlingensiepen, Bovenden; Reimar Schlingensiepen; Georg-Ferdinand Schlingensiepen, both of Göttingen, all of (DE)

(73) Assignee: Biognostik Gesellscahft Für Biomokekulare Diagnostik mbH, Götingen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/666,341

(22) PCT Filed: Dec. 9, 1994

(86) PCT No.: PCT/EP94/04094

§ 371 Date: Aug. 15, 1996

§ 102(e) Date: Aug. 15, 1996

(87) PCT Pub. No.: WO95/17507

PCT Pub. Date: Jun. 29, 1995

(30) Foreign Application Priority Data

Dec. 23, 1993 (EP) .............................................. 93120710

(51) Int. Cl.[7] .......................... C07H 21/04; C12Q 1/68; C12N 15/85
(52) U.S. Cl. .......................... 435/6; 435/91.1; 435/325; 435/375; 536/24.5
(58) Field of Search .......................... 435/6, 91.1, 325, 435/3, 172.1, 172.3; 536/23.1, 23.2, 24.5; 514/44

(56) References Cited

U.S. PATENT DOCUMENTS 5,599,704 A * 2/1997 Thompsen et al. ......... 435/325

FOREIGN PATENT DOCUMENTS

| WO | WO 92 13063 | 8/1992 |
| WO | WO 92 19732 | 11/1992 |
| WO | WO 93 09788 | 5/1993 |

OTHER PUBLICATIONS

Branch, A good antisense molecule is hard to find, TIBS, vol. 23, pp. 45–50, Feb. 1998.*
Agrawal, Antisense oligonucleotides:towards clinical trials, TIBTECH, vol. 14, pp. 376–387, Oct. 1996.*
Gewirtz et al., Facilitating oligonucleotide delivery: helping antisense deliver on its promise, PNAS, vol. 93, pp. 3161–3163, Apr. 1996.*
Gerwirtz et al. PNAS 93:3161–3163 (1996).*
Rojanasakul et al. Adv. Arag. Delivery Mer. 18:115–131 (1996).*
Proceedings of the American Association for Cancer Research, vol. 32, Mar. 1991, p. 433, Brysch, W. et al. "Inhibiting c–erbB–2 overexpression in human mammary carcinoma cells with phosphorothioate oligodeoxynucleotides".
Gene Regulation: Biology of Antisens RNA and DNA; K.H. Schlingensiepen & W. Brysch; 1992; pp. 317–328; Phosphorothioate oligomers: Inhibitors of Oncogene Expression in Tumor Cells and Tools for Gene Function Analysis.
Science, vol. 230, Dec. 6, 1985, Lancaster, PA; pp. 1132–1139 Coussens, L. et al.; "Tyrosine Kinase Receptor with Extensive Homology to EGF Receptor Shares Chromosomal Location With Neu Oncogene".

* cited by examiner

Primary Examiner—Andrew Wang
(74) Attorney, Agent, or Firm—Jacobson Holman, PLLC

(57) ABSTRACT

The present invention is related to an antisense-nucleic acid or effective derivatives thereof hybridizing with an area of the messenger RNA (mRNA) or the DNA, encoding the $p185^{erbB-2}$ receptor (also termed c-erbB-2, HER2 or neu), a pharmaceutical composition, comprising an antisense nucleic acid or effective derivatives thereof hybridizing with an area of the messenger RNA (mRNA) or the DNA, encoding the c-erbB-2 receptor as well as the use of said antisense nucleic acids and derivatives thereof for the manufacturing of a pharmaceutical composition for the treatment of neoplasms and/or immune diseases and/or diseases involving pathological angiogenesis.

5 Claims, No Drawings

US 6,365,345 B1

ANTISENSE NUCLEIC ACIDS FOR THE PREVENTION AND TREATMENT OF DISORDERS IN WHICH EXPRESSION OF C-ERBB PLAYS A ROLE

The present invention is related to an antisense-nucleic acid or effective derivatives thereof hybridizing with an area of the messenger RNA (mRNA) or the DNA, encoding the $p185^{erbB-2}$ receptor (also termed c-erbB-2, HER2 or neu), a pharmaceutical composition, comprising an antisense nucleic acid or effective derivatives thereof hybridizing with an area of the messenger RNA (mRNA) or the DNA, encoding the c-erbB-2 receptor as well as the use of said antisense nucleic acids and derivatives thereof for the manufacturing of a pharmaceutical composition for the treatment of neoplasms and/or immune diseases and/or diseases involving pathological angiogenesis.

ErbB-2 is a putative growth factor receptor with an intracellular tyrosine kinase activity that is amplified and/or overexpressed by tumor cells in a variety of neoplasms including breast cancer, lung cancer, esophageal and gastric cancer, bile duct carcinoma, bladder cancer and ovarian cancer.

In breast carcinoma patients, an amplification and overexpression of the c-erbB-2 gene in the tumor tissue has been shown to correlate with a poor clinical prognosis. Overexpression of $p185^{erbB-2}$ in non-small-cell lung carcinoma has been shown to impart resistance to a number of chemotherapeutic agents.

WO 93/09788 discloses a method for inhibiting the proliferation of cells which contain an erb B2/neu gene site. The method involves administering a therapeutic dose of an oligonucleotide which is capable of forming a colinear triplex with the promoter region of the erb B2/neu gene.

WO 92/19732 discloses sense and antisense oligonucleotides, namely closed oligonucleotides. These compounds may be used pharmacologically as sense or antisense molecules. It is generally described the therapeutic use of oligonucleotides as sense or antisense agents.

WO 92/13063 discloses a method for effecting expression of growth factors and growth factor receptors in cells or in multicellular animals and methods for testing compounds as effectors of transcription of growth factors and growth factor receptors.

The article "Chemically Modified Oligodeoxynucleotide Analogs as Regulators of Viral and Cellular Gene Expression" in Gene Regulation: Biology of Antisense RNA and DNA discloses in general the use of chemically modified oligonucleotides in the antisense technology.

It is an object of the present invention to provide a compound for the treatment of neoplasms and/or immune diseases and/or diseases involving pathological angiogenesis.

The c-erbB-2 antisense-oligonucleotide of the invention solving the problem addressed above have the sequences as disclosed in the sequence listing under Seq. ID No. 1–105, having a DNA- or RNA-type structure. The control oligonucleotide has the sequence as disclosed in the sequence listing under Seq. ID No 106, having a DNA- or RNA-type structure.

The antisense nucleic acids of the invention, were able to strongly inhibit the expression of the $p185^{erbB-2}$ protein, tyrosine kinase activity and cell growth in a variety of tumor cells including breast cancer cells. Untransformed normal fibroblasts were not growth inhibited by the anti-c-erbB-2 antisense compounds. This suggests that $p185^{erbB-2}$ plays a pathogenetic role in the growth of the above mentioned tumor cells.

Furthermore, surprisingly, the immune response to a variety of neoplasms was significantly increased by the use of the antisense nucleic acids of the invention. Immune cell growth and activity was stimulated in co-culture assays culturing tumor cells and peripheral blood monocytes together.

Surprisingly, the antisense nucleic acids of the invention, also acted as strong inhibitors of angiogenesis. This suggests, that either the secreted truncated form of the c-erbB-2 protein or the full receptor protein may play a causal role in pathological neoangiogenesis.

According to the invention antisense nucleic acids or effective derivatives thereof which hybridize with an area of the mRNA or DNA coding for $p185^{erbB-2}$ can effectively treat the diseases addressed above. The antisense nucleic acid is able to hybridize with regions of $p185^{erbB-2}$ mRNA. It is understood by the skilled person that fragments of the antisense nucleic acids and antisense nucleic acids containing these sequences work according to the invention so long as production of $p185^{erbB-2}$ is reduced or inhibited.

According to the invention the antisense-oligonucleotides are obtainable by solid phase synthesis using phosphite triester chemistry by growing the nucleotide chain in 3'-5' direction in that the respective nucleotide is coupled to the first nucleotide which is covalently attached to the solid phase comprising the steps of cleaving 5' DMT protecting group of the previous nucleotide, adding the respective nucleotide for chain propagation, modifying the phosphite group subsequently cap unreacted 5'-hydroxyl groups and cleaving the oligonucleotide from the solid support, followed by working up the synthesis product.

The chemical structures of oligodeoxy-ribonucleotides are given in FIG. 1 as well as the respective structures of antisense oligo-ribonucleotides are given in FIG. 2. The oligonucleotide chain is to be understood as a detail out of a longer nucleotide chain.

In FIG. 1, lit. B means an organic base such as adenine (A), guanine (G), cytosine (C) and thymine (T) which are coupled via N9(A,G) or N1(D,T) to the desoxyribose. The sequence of the bases is the reverse complement of the genetic target sequence (mRNA-sequence). The modifications used are 1. Oligodeoxy-ribonucleotides where all $R^1$ are substituted by
    1.1 $R^1=O$
    1.2 $R^1=S$
    1.3 $R^1=F$
    1.4 $R^1=CH_3$
    1.5 $R^1=OEt$
2. Oligodeoxy-ribonucleotides where $R^1$ is varied at the internucleotide phosphates within one oligonucleotide

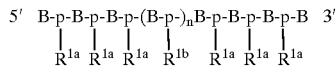

where
B=deoxy-ribonucleotide dA, dC, dG or dT depending on gene sequence
p=internucleotide phosphate
n=an oligodeoxy-ribonucleotide stretch of length 6–20 bases

| 2.1 | $R^{1a} = S$;    | $R^{1b} = O$   |
| --- | ---------------- | -------------- |
| 2.2 | $R^{1a} = CH_3$; | $R^{1b} = O$   |
| 2.3 | $R^{1a} = S$;    | $R^{1b} = CH_3$ |
| 2.4 | $R^{1a} = CH_3$; | $R^{1b} = S$   |

3. Oligodeoxy-ribonucleotides where $R^1$ is alternated at the internucleotide phosphates within one oligonucleotide

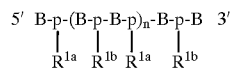

where B=deoxy-ribonucleotide dA, dC, dG or dT depending on gene sequence
p=internucleotide phosphate
n=an oligodeoxy-ribodinucleotide stretch of length 4–12 dinucleotides

| 3.2 | $R^{1a} = S$;    | $R^{1b} = O$    |
| --- | ---------------- | --------------- |
| 3.2 | $R^{1a} = CH_3$; | $R^{1b} = O$    |
| 3.3 | $R^{1a} = S$;    | $R^{1b} = CH_3$ |

4. Any of the compounds 1.1–1.5; 2.1–2.4; 3.1–3.3 coupled at $R^2$ with the following compounds which are covalently coupled to increased cellular uptake
4.1 cholesterol
4.2 poly(L)lysine
4.3 transferrin
5. Any of the compounds 1.1–1.5; 2.1–2.4; 3.1–3.3 coupled at $R^3$ with the following compounds which are covalently coupled to increase cellular uptake
5.1 cholesterol
5.2 poly(L)lysine
5.3 transferrin In the case of the RNA-oligonucleotides (FIG. 2) are the basis (adenine (A), guanine (G), cytosine (C), uracil (U)) coupled via N9 (A,G) or N1 (C,U) to the ribose. The sequence of the basis is the reverse complement of the genetic target sequence (mRNA-sequence). The modifications in the oligonucleotide sequence used are as follows
6. Oligo-ribonucleotides where all $R^1$ are substituted by
6.1 $R^1=O$
6.2 $R^1=S$
6.3 $R^1=F$
6.4 $R^1=CH_3$
6.5 $R^1=OEt$
7. Oligo-ribonucleotides where $R^1$ is varied at the internucleotide phosphates within one oligonucleotide

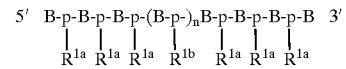

where
B=ribonucleotide A, C, G or T depending on gene sequence
p=internucleotide phosphate
n=an oligo-ribonucleotide stretch of length 4–20 bases

| 7.1 | $R^{1a} = S$;    | $R^{1b} = O$    |
| --- | ---------------- | --------------- |
| 7.2 | $R^{1a} = CH_3$; | $R^{1b} = O$    |
| 7.3 | $R^{1a} = S$;    | $R^{1b} = CH_3$ |
| 7.4 | $R^{1a} = CH_3$; | $R^{1b} = S$    |

8. Oligo-ribonucleotides where $R^1$ is alternated at the internucleotide phosphates within one oligonucleotide

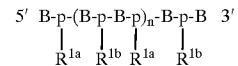

where
B=ribonucleotide A, C, G or T depending on gene sequence
p=internucleotide phosphate
n=an oligo-ribodinucleotide stretch of length 4–12 dinucleotides

| 8.2 | $R^{1a} = S$;    | $R^{1b} = O$    |
| --- | ---------------- | --------------- |
| 8.3 | $R^{1a} = CH_3$; | $R^{1b} = O$    |
| 8.4 | $R^{1a} = S$;    | $R^{1b} = CH_3$ |

9. Any of the compounds 6.1–6.5; 7.1–7.4; 8.1–3.3 coupled at $R^2$ with the following compounds which are covalently coupled to increase cellular uptake
9.1 cholesterol
9.2 poly(L)lysine
9.3 transferrin
10. Any of the compounds 6.1–6.5; 7.1–7.4; 8.1–8.3 coupled at $R^3$ the following compounds are covalently coupled to increased cellular uptake
10.1 cholesterol
10.2 poly (L) lysine
10.3 transferrin
11. Any of the compounds 6.1–6.5; 7.1–7.4; 8.1–8.3; 9.1–9.3; 10.1–10.3 where all $R^4$ are substituted by
11.1 $R^4=O$
11.2 $R^4=F$
11.3 $R^4=CH_3$ In a preferred embodiment of the oligonucleotides of the invention they are phosphorothioate derivatives, having a DNA- or RNA-type structure.

It is possible that one single individual sequence as mentioned above works as an antisense nucleic acid or oligonucleotide structure according to the invention. However, it is also possible that one strand of nucleotides comprises more than one of the sequences as mentioned above directly covalently linked or with other nucleotides covalently linked in between. Preferably, individual oligo-nucleotides are addressed.

In a preferred embodiment of these oligo-nucleotides they are phosphorothioate derivatives.

Modifications of the antisense-oligonucleotides are advantageous since they are not as fast destroyed by endogenous factors when applied as this is valid for naturally occurring nucleotide sequences. However, it is understood by the skilled person that also naturally occurring nucleotides having the disclosed sequence can be used according to the invention. In a very preferred embodiment the modification is a phosphorothioate modification.

The synthesis of the oligodeoxy-nucleotide of the invention is described as an example in a greater detail as follows.

Oligodeoxy-nucleotides were synthesized by stepwise 5'-addition of protected nucleosides using phosphite triester chemistry. The nucleotide A was introduced as 5'dimethoxytrityl-deoxyadenosine(N-benzoyl)-N,N'-diisopropyl-2-cyano-ethyl phosphoramidite (0.1 M); C was introduced by a 5'-dimethoxytrityl-deoxycytidine ($N^4$-benzoyl)-N,N'-diisopropyl-2-cyanoethyl phosphoramidite; G was introduced as 5'-dimethoxytrityl-deoxyguanosine ($N^8$-isobutyryl)-N,N'-diisopropyl-2-cyanoethyl phosphoramidite and the T was introduced as 5'-dimethoxytrityl-deoxythymidine-N,N'-diisopropyl-2-cyanoethyl phosphoramidite. The nucleosides were preferably applied in 0.1 M concentration dissolved in acetonitrile.

Synthesis was performed on controlled pore glass particles of approximately 150 µm diameter (pore diameter 500 Å) to which the most 3' nucleoside is covalently attached via a long-chain alkylamine linker (average loading 30 µmol/g solid support).

The solid support was loaded into a cylindrical synthesis column, capped on both ends with filters which permit adequate flow of reagents but hold back the solid synthesis support. Reagents were delivered and withdrawn from the synthesis column using positive pressure of inert gas. The nucleotides were added to the growing oligonucleotide chain in 3'->5' direction. Each nucleotide was coupled using one round of the following synthesis cycle:

Cleave 5'DMT (dimethoxytrityl) protecting group of the previous nucleotide with 3-chloroacetic acid in dichloromethane followed by washing the column with anhydrous acetonitrile.

Then simultaneously one of the bases in form of their protected derivative depending on the sequence was added plus tetrazole in acetonitrile. After reaction the reaction mixture has been withdrawn and the phosphite was oxidized with a mixture of sulfur ($S_8$) in carbon disulfide/pyridine/triethylamine. After the oxidation reaction the mixture was withdrawn and the column was washed with acetonitrile. The unreacted 5'-hydroxyl groups were capped with simultaneous addition of 1-methylimidazole and acetic anhydride/lutidine/tetrahydrofuran. Thereafter, the synthesis column was washed with acetonitrile and the next cycle was started.

The work up procedure and purification of the synthesis products occurred as follows.

After the addition of the last nucleotide the deoxynucleotides were cleaved from the solid support by incubation in ammonia solution. Exocyclic base protecting groups were removed by further incubation in ammonia. Then the ammonia was evaporated under vacuum. Full-length synthesis products still bearing the 5'DMT protecting group were separated from shorter failure contaminants using reverse phase high performance liquid chromatography on silica $C_{18}$ stationary phase. Eluents from the product peak were collected, dried under vacuum and the 5'-DMT protecting group cleaved by incubation in acetic acid which was evaporated thereafter under vacuum. The synthesis products were solubilized in the deionized water and extracted three times with diethylether. Then the products were dried in vacuo. Another HPLC-AX chromatography was performed and the eluents from the product peak were dialyzed against excess of Trisbuffer as well as a second dialysis against deionized water. The final products were lyophilized and stored dry.

The antisense-nucleic acid of the invention can be used as pharmaceutical composition or medicament. This medicament can be used for treating neoplasms and/or immune diseases and/or diseases involving pathological angiogenesis in which the expression of c-erbB-2 derived receptor protein or truncated $p185^{c-erbB2}$ is of relevance for the pathogenicity. It can be used to reduce neoplastic cell growth in cells expressing $p185^{c-erbB2}$, to reverse resistance of tumor cells to the immune-response, to inhibit pathological angiogenesis and to stimulate the immune system.

The antisense nucleic acids of the invention are intermediate products of the pharmaceutical composition or medicament of the invention. The pharmaceutical composition may comprise besides the effective compound(s) suitable carrier agents, solvents and other ingredients known in the art for producing medicaments. Preferably, these agents facilitate the administration of the pharmaceutical composition of the invention. Typically, the pharmaceutical composition is administered as i.v. infusion or i.v. bolus injection. The amount of the active ingredient to be administered is typically in the range of 0.2–50 mg of the oligonucleotide per kg body weight per day, in particular 1–12 mg/kg body weight per day.

In principal the compound which can be used as an active compound in the pharmaceutical composition can be used as a diagnostic tool for evaluating whether the respective genes are expressed. Typically, radio active labelled nucleotides are hybridized by the method of northern blotting which is well-known in the art or in situ with a sample to be examined. The degree of hybridization is a measure for the degree of expression of the respective genes.

The effect of c-erbB2 specific antisense-oligonucleotides on neoplastic cell growth was investigated. It was demonstrated that antisense oligodeoxynucleotides as well as phosphorothioate modified nucleic acids, complementary to c-erbB2 mRNA could specifically inhibit $p185^{c-erbB2}$ protein expression and could to a significant amount reduce cell proliferation in breast cancer cells, ovarian carcinoma cells and bladder cancer cells. Also, it could be shown that protein synthesis and S6 kinase activity were strongly reduced in tumor cells, treated with the antisense nucleic acid.

Furthermore, the immune response to a variety of neoplasms was significantly increased by the use of the antisense nucleic acids described below. Lymphocyte growth and activity was stimulated in co-culture assays culturing tumor cells and peripheral blood monocytes together.

Furthermore, the antisense nucleic acids described above, also acted as inhibitors of angiogenesis.

What is claimed is:

1. An antisense oligonucleotide, which will hybridize with an area of the messenger RNA (mRNA) and/or DNA encoding c-erbB-2, selected from the group consisting of SEQ. ID NOS. 1–105, wherein said antisense oligonucleotide has a DNA- or RNA-type structure.

2. The antisense oligonucleotide of claim 1 wherein the oligonucleotides are modified as phosphorothioate derivatives.

3. A method of making an antisense oligonucleotide according to claim 1 obtained by solid phase synthesis using phosphite triester chemistry by growing the nucleotide chain in 3'-5' direction, in that the respective nucleotide is coupled to the first nucleotide which is covalently attached to the solid phase, comprising the steps of cleaving 5' DMT protecting group of the previous nucleotide, adding the respective nucleotide for chain propagation, modifying phosphite groups, subsequently capping unreacted 5'-hydroxyl groups, and cleaving the oligonucleotide from the solid support, followed by working up the synthesis product.

4. A method for inhibiting expression of c-erbB-2 in cells or in cells in culture comprising delivering the antisense oligonucleotide of claim 1 to said cells such that it inhibits c-erbB-2 expression.

5. A method of assaying for c-erbB-2 gene expression comprising the steps of:

radioactive labeling of the antisense oligonucleotide of claim 1 and combining a radioactive labeled nucleic acid with a sample, whereby, the degree of hybridization of the radioactive labeled oligonucleotide is a measure of the degree of expression of the gene encoding c-erbB-2.

* * * * *

```
                            SEQUENCE LISTING (1) GENERAL INFORMATION:

(iii) NUMBER OF SEQUENCES:  106

(2) INFORMATION FOR SEQ ID NO: 1:

(i) SEQUENCE CHARACTERISTICS:
          (A) LENGTH: 14 base pairs
          (B) TYPE: nucleic acid
          (C) STRANDEDNESS: unknown
          (D) TOPOLOGY: unknown (ii) MOLECULE TYPE: DNA (genomic)

(iii) ANTI-SENSE: YES (xi) SEQUENCE DESCRIPTION: SEQ ID NO: 1:

TTCATGTCTG TGCC                                                       14

(2) INFORMATION FOR SEQ ID NO: 2:

(i) SEQUENCE CHARACTERISTICS:
          (A) LENGTH: 14 base pairs
          (B) TYPE: nucleic acid
          (C) STRANDEDNESS: unknown
          (D) TOPOLOGY: unknown (ii) MOLECULE TYPE: DNA (genomic)

(iii) ANTI-SENSE: YES (xi) SEQUENCE DESCRIPTION: SEQ ID NO: 2:

GTAGGTGAGT TCCA                                                       14

(2) INFORMATION FOR SEQ ID NO: 3:

(i) SEQUENCE CHARACTERISTICS:
          (A) LENGTH: 14 base pairs
          (B) TYPE: nucleic acid
          (C) STRANDEDNESS: unknown
          (D) TOPOLOGY: unknown (ii) MOLECULE TYPE: DNA (genomic)

(iii) ANTI-SENSE: YES (xi) SEQUENCE DESCRIPTION: SEQ ID NO: 3:

GTTGTGAGCG ATGA                                                       14

(2) INFORMATION FOR SEQ ID NO: 4:

(i) SEQUENCE CHARACTERISTICS:
          (A) LENGTH: 18 base pairs
          (B) TYPE: nucleic acid
          (C) STRANDEDNESS: unknown
          (D) TOPOLOGY: unknown (ii) MOLECULE TYPE: DNA (genomic)

(iii) ANTI-SENSE: YES (xi) SEQUENCE DESCRIPTION: SEQ ID NO: 4:

CATAGTTGTC CTCAAAGA                                                   18
```

(2) INFORMATION FOR SEQ ID NO: 5:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 5:

GGCATAGTTG TCCT                                               14

(2) INFORMATION FOR SEQ ID NO: 6:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 6:

CATTGTCTAG CACG                                               14

(2) INFORMATION FOR SEQ ID NO: 7:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 7:

CTCCATTGTC TAGC                                               14

(2) INFORMATION FOR SEQ ID NO: 8:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 8:

GTATTGTTCA GCGG                                               14

(2) INFORMATION FOR SEQ ID NO: 9:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 9:

TCAAGATCTC TGTGAG                                                            16

(2) INFORMATION FOR SEQ ID NO: 10:

(i) SEQUENCE CHARACTERISTICS:
              (A) LENGTH: 16 base pairs
              (B) TYPE: nucleic acid
              (C) STRANDEDNESS: unknown
              (D) TOPOLOGY: unknown (ii) MOLECULE TYPE: DNA (genomic)

(iii) ANTI-SENSE: YES (xi) SEQUENCE DESCRIPTION: SEQ ID NO: 10:

CACAAAATCG TGTCCT                                                            16

(2) INFORMATION FOR SEQ ID NO: 11:

(i) SEQUENCE CHARACTERISTICS:
              (A) LENGTH: 16 base pairs
              (B) TYPE: nucleic acid
              (C) STRANDEDNESS: unknown
              (D) TOPOLOGY: unknown (ii) MOLECULE TYPE: DNA (genomic)

(iii) ANTI-SENSE: YES (xi) SEQUENCE DESCRIPTION: SEQ ID NO: 11:

TCCTTCCACA AAATCG                                                            16

(2) INFORMATION FOR SEQ ID NO: 12:

(i) SEQUENCE CHARACTERISTICS:
              (A) LENGTH: 14 base pairs
              (B) TYPE: nucleic acid
              (C) STRANDEDNESS: unknown
              (D) TOPOLOGY: unknown (ii) MOLECULE TYPE: DNA (genomic)

(iii) ANTI-SENSE: YES (xi) SEQUENCE DESCRIPTION: SEQ ID NO: 12:

GTGGAAGATG TCCT                                                              14

(2) INFORMATION FOR SEQ ID NO: 13:

(i) SEQUENCE CHARACTERISTICS:
              (A) LENGTH: 16 base pairs
              (B) TYPE: nucleic acid
              (C) STRANDEDNESS: unknown
              (D) TOPOLOGY: unknown (ii) MOLECULE TYPE: DNA (genomic)

(iii) ANTI-SENSE: YES (xi) SEQUENCE DESCRIPTION: SEQ ID NO: 13:

TCTTGTGGAA GATGTC                                                            16

(2) INFORMATION FOR SEQ ID NO: 14:

(i) SEQUENCE CHARACTERISTICS:
              (A) LENGTH: 16 base pairs (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 14:

TCTATCAGTG TGAGAG                                                    16

(2) INFORMATION FOR SEQ ID NO: 15:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 15:

GGTTGGTGTC TATC                                                      14

(2) INFORMATION FOR SEQ ID NO: 16:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 16:

ACATCGGAGA ACAG                                                      14

(2) INFORMATION FOR SEQ ID NO: 17:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 17:

CCTTACACAT CGGA                                                      14

(2) INFORMATION FOR SEQ ID NO: 18:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 18:

ACAATCCTCA GAACTC                                                    16

(2) INFORMATION FOR SEQ ID NO: 19:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 19:

GCTCTGACAA TCCT                                        14

(2) INFORMATION FOR SEQ ID NO: 20:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 20:

TGGTTGAAGT GGAG                                        14

(2) INFORMATION FOR SEQ ID NO: 21:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 21:

CTGTGGTTGA AGTG                                        14

(2) INFORMATION FOR SEQ ID NO: 22:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 22:

GTTGTAGGTG ACCA                                        14

(2) INFORMATION FOR SEQ ID NO: 23:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 23:

CTGTGTTGTA GGTG                                                     14

(2) INFORMATION FOR SEQ ID NO: 24:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 24:

GACTCAAACG TGTC                                                     14

(2) INFORMATION FOR SEQ ID NO: 25:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 25:

CATGGACTCA AACG                                                     14

(2) INFORMATION FOR SEQ ID NO: 26:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 26:

CGAATGTATA CCGG                                                     14

(2) INFORMATION FOR SEQ ID NO: 27:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 27:

CCGAATGTAT ACCG                                                     14

(2) INFORMATION FOR SEQ ID NO: 28:

(i) SEQUENCE CHARACTERISTICS:

(A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 28:

GCCGAATGTA TACC                                                              14

(2) INFORMATION FOR SEQ ID NO: 29:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 29:

GTAGTTGTAG GGAC                                                              14

(2) INFORMATION FOR SEQ ID NO: 30:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 30:

TAGAAAGGTA GTTGTAGG                                                          18

(2) INFORMATION FOR SEQ ID NO: 31:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 31:

GTAGAAAGGT AGTTGTAG                                                          18

(2) INFORMATION FOR SEQ ID NO: 32:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 32:

CGTAGAAAGG TAGTTG                                                          16

(2) INFORMATION FOR SEQ ID NO: 33:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 33:

CCGTAGAAAG GTAG                                                            14

(2) INFORMATION FOR SEQ ID NO: 34:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 34:

GACCATAGCA CACT                                                            14

(2) INFORMATION FOR SEQ ID NO: 35:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 35:

GGATATTGGC ACTG                                                            14

(2) INFORMATION FOR SEQ ID NO: 36:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 36:

CCTGGATATT GGCA                                                            14

(2) INFORMATION FOR SEQ ID NO: 37:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 37:

GCTCCCAAAG ATCT                                                         14

(2) INFORMATION FOR SEQ ID NO: 38:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 38:

CCCATCAAAG CTCT                                                         14

(2) INFORMATION FOR SEQ ID NO: 39:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 39:

CAAACACTTG GAGC                                                         14

(2) INFORMATION FOR SEQ ID NO: 40:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 40:

GTCTCAAACA CTTGGA                                                       16

(2) INFORMATION FOR SEQ ID NO:41:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 41:

GAGTCTCAAA CACTTG                                                       16

(2) INFORMATION FOR SEQ ID NO: 42:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 42:

GTAACCTGTG ATCTCT                                                    16

(2) INFORMATION FOR SEQ ID NO: 43:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 43:

GGTAACCTGT GATC                                                      14

(2) INFORMATION FOR SEQ ID NO: 44:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 44:

GTATAGGTAA CCTGTG                                                    16

(2) INFORMATION FOR SEQ ID NO: 45:

(i) SEQUENCE CHARACTERISTICS:
            (A) LENGTH: 18 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 45:

TGAGATGTAT AGGTAACC                                                  18

(2) INFORMATION FOR SEQ ID NO: 46:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 46:

TGCTGAGATG TATAGG                    16

(2) INFORMATION FOR SEQ ID NO: 47:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 47:

CCATGCTGAG ATGT                      14

(2) INFORMATION FOR SEQ ID NO: 48:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 48:

GGATTACTTG CAGG                      14

(2) INFORMATION FOR SEQ ID NO:49:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 49:

TGTTATGGTG GATGAG                    16

(2) INFORMATION FOR SEQ ID NO: 50:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 50:

GGTGTTATGG TGGA                      14

(2) INFORMATION FOR SEQ ID NO: 51:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 51:

GCAGTTGACA CACT                                                             14

(2) INFORMATION FOR SEQ ID NO: 52:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 52:

AGTACTCGGC ATTC                                                             14

(2) INFORMATION FOR SEQ ID NO: 53:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 53:

CATTCACATA CTCCCT                                                           16

(2) INFORMATION FOR SEQ ID NO: 54:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 54:

TCCAAAACAG GTCACT                                                           16

(2) INFORMATION FOR SEQ ID NO: 55:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 55:

GGTCCTTATA GTGG                                                             14

(2) INFORMATION FOR SEQ ID NO: 56:

(i) SEQUENCE CHARACTERISTICS:
           (A) LENGTH: 14 base pairs
           (B) TYPE: nucleic acid
           (C) STRANDEDNESS: unknown
           (D) TOPOLOGY: unknown (ii) MOLECULE TYPE: DNA (genomic)

(iii) ANTI-SENSE: YES (xi) SEQUENCE DESCRIPTION: SEQ ID NO: 56:

CAGAATGCCA ACCA                                                              14

(2) INFORMATION FOR SEQ ID NO: 57:

(i) SEQUENCE CHARACTERISTICS:
           (A) LENGTH: 14 base pairs
           (B) TYPE: nucleic acid
           (C) STRANDEDNESS: unknown
           (D) TOPOLOGY: unknown (ii) MOLECULE TYPE: DNA (genomic)

(iii) ANTI-SENSE: YES (xi) SEQUENCE DESCRIPTION: SEQ ID NO: 57:

ACGAGAATGC CAAC                                                              14

(2) INFORMATION FOR SEQ ID NO: 58:

(i) SEQUENCE CHARACTERISTICS:
           (A) LENGTH: 14 base pairs
           (B) TYPE: nucleic acid
           (C) STRANDEDNESS: unknown
           (D) TOPOLOGY: unknown (ii) MOLECULE TYPE: DNA (genomic)

(iii) ANTI-SENSE: YES (xi) SEQUENCE DESCRIPTION: SEQ ID NO: 58:

GATCCCAAAG ACCA                                                              14

(2) INFORMATION FOR SEQ ID NO: 59:

(i) SEQUENCE CHARACTERISTICS:
           (A) LENGTH: 14 base pairs
           (B) TYPE: nucleic acid
           (C) STRANDEDNESS: unknown
           (D) TOPOLOGY: unknown (ii) MOLECULE TYPE: DNA (genomic)

(iii) ANTI-SENSE: YES (xi) SEQUENCE DESCRIPTION: SEQ ID NO: 59:

TCGCTTGATG AGGA                                                              14

(2) INFORMATION FOR SEQ ID NO: 60:

(i) SEQUENCE CHARACTERISTICS:
           (A) LENGTH: 14 base pairs
           (B) TYPE: nucleic acid
           (C) STRANDEDNESS: unknown
           (D) TOPOLOGY: unknown (ii) MOLECULE TYPE: DNA (genomic)

(iii) ANTI-SENSE: YES

-continued (xi) SEQUENCE DESCRIPTION: SEQ ID NO: 60:

CATCGTGTAC TTCC                                                              14

(2) INFORMATION FOR SEQ ID NO: 61:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 61:

GCATCGTGTA CTTC                                                              14

(2) INFORMATION FOR SEQ ID NO: 62:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 62:

ACTGTGCCAA AAGC                                                              14

(2) INFORMATION FOR SEQ ID NO: 63:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 63:

CTTGTAGACT GTGC                                                              14

(2) INFORMATION FOR SEQ ID NO: 64:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 64:

CCCTTGTAGA CTGT                                                              14

(2) INFORMATION FOR SEQ ID NO: 65:

(i) SEQUENCE CHARACTERISTICS:
        (A) LENGTH: 16 base pairs
        (B) TYPE: nucleic acid
        (C) STRANDEDNESS: unknown (D) TOPOLOGY: unknown (ii) MOLECULE TYPE: DNA (genomic)

(iii) ANTI-SENSE: YES (xi) SEQUENCE DESCRIPTION: SEQ ID NO: 65:

TCAACACTTT GATGGC                                                    16

(2) INFORMATION FOR SEQ ID NO: 66:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 66:

CCCTCAACAC TTTG                                                      14

(2) INFORMATION FOR SEQ ID NO: 67:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 67:

GTGTTTTCCC TCAACA                                                    16

(2) INFORMATION FOR SEQ ID NO: 68:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 68:

GTATGCTTCG TCTAAG                                                    16

(2) INFORMATION FOR SEQ ID NO: 69:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 69:

CGTATGCTTC GTCT                                                      14

```
(2) INFORMATION FOR SEQ ID NO: 70:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 70:

CCATCACGTA TGCT                                              14

(2) INFORMATION FOR SEQ ID NO: 71:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 71:

GCATAAGCTG TGTC                                              14

(2) INFORMATION FOR SEQ ID NO: 72:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 72:

CATGGTCTAA GAGG                                              14

(2) INFORMATION FOR SEQ ID NO: 73:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 73:

CAATCTGCAT ACACCA                                            16

(2) INFORMATION FOR SEQ ID NO: 74:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES
```

(xi) SEQUENCE DESCRIPTION: SEQ ID NO: 74:

GGCAATCTGC ATAC                                                         14

(2) INFORMATION FOR SEQ ID NO: 75:

(i) SEQUENCE CHARACTERISTICS:
           (A) LENGTH: 14 base pairs
           (B) TYPE: nucleic acid
           (C) STRANDEDNESS: unknown
           (D) TOPOLOGY: unknown (ii) MOLECULE TYPE: DNA (genomic)

(iii) ANTI-SENSE: YES (xi) SEQUENCE DESCRIPTION: SEQ ID NO: 75:

CTGTCTCGTC AATG                                                         14

(2) INFORMATION FOR SEQ ID NO: 76:

(i) SEQUENCE CHARACTERISTICS:
           (A) LENGTH: 16 base pairs
           (B) TYPE: nucleic acid
           (C) STRANDEDNESS: unknown
           (D) TOPOLOGY: unknown (ii) MOLECULE TYPE: DNA (genomic)

(iii) ANTI-SENSE: YES (xi) SEQUENCE DESCRIPTION: SEQ ID NO: 76:

CATAACTCCA CACATC                                                       16

(2) INFORMATION FOR SEQ ID NO: 77:

(i) SEQUENCE CHARACTERISTICS:
           (A) LENGTH: 16 base pairs
           (B) TYPE: nucleic acid
           (C) STRANDEDNESS: unknown
           (D) TOPOLOGY: unknown (ii) MOLECULE TYPE: DNA (genomic)

(iii) ANTI-SENSE: YES (xi) SEQUENCE DESCRIPTION: SEQ ID NO: 77:

AGTCACACCA TAACTC                                                       16

(2) INFORMATION FOR SEQ ID NO: 78:

(i) SEQUENCE CHARACTERISTICS:
           (A) LENGTH: 16 base pairs
           (B) TYPE: nucleic acid
           (C) STRANDEDNESS: unknown
           (D) TOPOLOGY: unknown (ii) MOLECULE TYPE: DNA (genomic)

(iii) ANTI-SENSE: YES (xi) SEQUENCE DESCRIPTION: SEQ ID NO: 78:

ACAGTCACAC CATAAC                                                       16

(2) INFORMATION FOR SEQ ID NO: 79:

(i) SEQUENCE CHARACTERISTICS:
           (A) LENGTH: 14 base pairs
           (B) TYPE: nucleic acid (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 79:

CCCCAAAAGT CATC                                                          14

(2) INFORMATION FOR SEQ ID NO: 80:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 80:

TCGTAAGGTT TGGC                                                          14

(2) INFORMATION FOR SEQ ID NO: 81:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 81:

GATCCCATCG TAAG                                                          14

(2) INFORMATION FOR SEQ ID NO: 82:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 82:

CAATGGTGCA GATG                                                          14

(2) INFORMATION FOR SEQ ID NO: 83:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 83:

GACATCAATG GTGC                                                          14

(2) INFORMATION FOR SEQ ID NO: 84:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 84:

GTAGACATCA ATGGTG                                             16

(2) INFORMATION FOR SEQ ID NO: 85:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 85:

CATGATCATG TAGACATC                                           18

(2) INFORMATION FOR SEQ ID NO: 86:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 86:

CCATGATCAT GTAGAC                                             16

(2) INFORMATION FOR SEQ ID NO: 87:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 87:

CATTTGACCA TGATCATG                                           18

(2) INFORMATION FOR SEQ ID NO: 88:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 88:

CCAACATTTG ACCATG                                                    16

(2) INFORMATION FOR SEQ ID NO: 89:

(i) SEQUENCE CHARACTERISTICS:
            (A) LENGTH: 18 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 89:

TCATCCAACA TTTGACCA                                                  18

(2) INFORMATION FOR SEQ ID NO: 90:

(i) SEQUENCE CHARACTERISTICS:
            (A) LENGTH: 18 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 90:

GAGTCAATCA TCCAACAT                                                  18

(2) INFORMATION FOR SEQ ID NO: 91:

(i) SEQUENCE CHARACTERISTICS:
            (A) LENGTH: 16 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 91:

CAGAGTCAAT CATCCA                                                    16

(2) INFORMATION FOR SEQ ID NO: 92:

(i) SEQUENCE CHARACTERISTICS:
            (A) LENGTH: 14 base pairs
            (B) TYPE: nucleic acid
            (C) STRANDEDNESS: unknown
            (D) TOPOLOGY: unknown (ii) MOLECULE TYPE: DNA (genomic)

(iii) ANTI-SENSE: YES (xi) SEQUENCE DESCRIPTION: SEQ ID NO: 92:

CCGACATTCA GAGT                                                      14

(2) INFORMATION FOR SEQ ID NO: 93:

(i) SEQUENCE CHARACTERISTICS:
            (A) LENGTH: 16 base pairs (B) TYPE: nucleic acid
          (C) STRANDEDNESS: unknown
          (D) TOPOLOGY: unknown (ii) MOLECULE TYPE: DNA (genomic)

(iii) ANTI-SENSE: YES (xi) SEQUENCE DESCRIPTION: SEQ ID NO: 93:

GAATTCAGAC ACCAAC                                                        16

(2) INFORMATION FOR SEQ ID NO: 94:

(i) SEQUENCE CHARACTERISTICS:
          (A) LENGTH: 14 base pairs
          (B) TYPE: nucleic acid
          (C) STRANDEDNESS: unknown
          (D) TOPOLOGY: unknown (ii) MOLECULE TYPE: DNA (genomic)

(iii) ANTI-SENSE: YES (xi) SEQUENCE DESCRIPTION: SEQ ID NO: 94:

GATGACCACA AAGC                                                          14

(2) INFORMATION FOR SEQ ID NO: 95:

(i) SEQUENCE CHARACTERISTICS:
          (A) LENGTH: 16 base pairs
          (B) TYPE: nucleic acid
          (C) STRANDEDNESS: unknown
          (D) TOPOLOGY: unknown (ii) MOLECULE TYPE: DNA (genomic)

(iii) ANTI-SENSE: YES (xi) SEQUENCE DESCRIPTION: SEQ ID NO: 95:

CCATCAAATA CATCGG                                                        16

(2) INFORMATION FOR SEQ ID NO: 96:

(i) SEQUENCE CHARACTERISTICS:
          (A) LENGTH: 18 base pairs
          (B) TYPE: nucleic acid
          (C) STRANDEDNESS: unknown
          (D) TOPOLOGY: unknown (ii) MOLECULE TYPE: DNA (genomic)

(iii) ANTI-SENSE: YES (xi) SEQUENCE DESCRIPTION: SEQ ID NO: 96:

TCACCATCAA ATACATCG                                                      18

(2) INFORMATION FOR SEQ ID NO: 97:

(i) SEQUENCE CHARACTERISTICS:
          (A) LENGTH: 14 base pairs
          (B) TYPE: nucleic acid
          (C) STRANDEDNESS: unknown
          (D) TOPOLOGY: unknown (ii) MOLECULE TYPE: DNA (genomic)

(iii) ANTI-SENSE: YES (xi) SEQUENCE DESCRIPTION: SEQ ID NO: 97:

CAACGTAGCC ATCA                                                          14

(2) INFORMATION FOR SEQ ID NO: 98:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 98:

ACGTCTTTGA CGAC                                          14

(2) INFORMATION FOR SEQ ID NO: 99:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 99:

CAAAAACGTC TTTGACGA                                  18

(2) INFORMATION FOR SEQ ID NO: 100:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 100:

GGCAAAAACG TCTTTG                                     16

(2) INFORMATION FOR SEQ ID NO: 101:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 101:

CAAAGGCAAA AACGTC                                     16

(2) INFORMATION FOR SEQ ID NO: 102:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

```
    (iii) ANTI-SENSE: YES (xi) SEQUENCE DESCRIPTION: SEQ ID NO: 102:

GTGTCAAGTA CTCG                                                    14

(2) INFORMATION FOR SEQ ID NO: 103:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 103:

GTAATAGAGG TTGTCG                                                  16

(2) INFORMATION FOR SEQ ID NO: 104:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 104:

CCCAGTAATA GAGG                                                    14

(2) INFORMATION FOR SEQ ID NO: 105:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 105:

CATGGTGCTC ACTG                                                    14

(2) INFORMATION FOR SEQ ID NO: 106:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(iii) ANTI-SENSE: YES (xi) SEQUENCE DESCRIPTION: SEQ ID NO: 106:

GTGCCTGTAC GTAC                                                    14
```